(12) United States Patent
Shchegrov et al.

(10) Patent No.: US 10,352,876 B2
(45) Date of Patent: *Jul. 16, 2019

(54) SIGNAL RESPONSE METROLOGY FOR SCATTEROMETRY BASED OVERLAY MEASUREMENTS

(71) Applicant: KLA—Tencor Corporation, Milpitas, CA (US)

(72) Inventors: Andrei V. Shchegrov, Campbell, CA (US); Stilian Ivanov Pandev, Santa Clara, CA (US); Jonathan M. Madsen, Los Altos, CA (US); Alexander Kuznetsov, Mountain View, CA (US); Walter Dean Mieher, Los Gatos, CA (US)

(73) Assignee: KLA—Tencor Corporation, Milpitas, CA (US)

( * ) Notice: Subject to any disclaimer, the term of this patent is extended or adjusted under 35 U.S.C. 154(b) by 374 days.

This patent is subject to a terminal disclaimer.

(21) Appl. No.: 14/704,840

(22) Filed: May 5, 2015

(65) Prior Publication Data

US 2015/0323316 A1 Nov. 12, 2015

Related U.S. Application Data

(60) Provisional application No. 61/991,395, filed on May 9, 2014.

(51) Int. Cl.
*G06N 20/00* (2019.01)
*G01N 21/95* (2006.01)
*G01B 11/27* (2006.01)

(52) U.S. Cl.
CPC ......... *G01N 21/9501* (2013.01); *G01B 11/27* (2013.01); *G06N 20/00* (2019.01)

(58) Field of Classification Search
None
See application file for complete search history.

(56) References Cited

U.S. PATENT DOCUMENTS

| 5,608,526 A | 3/1997 | Piwonka-Corle et al. |
| 5,859,424 A | 1/1999 | Norton et al. |

(Continued)

FOREIGN PATENT DOCUMENTS

| CN | 102478842 A | 5/2012 |
| EP | 1601931 B1 | 4/2011 |

OTHER PUBLICATIONS

International Search Report dated Aug. 27, 2015, for PCT Application No. PCT/US2015/029896 filed on May 8, 2015 by KLA—Tencor Corporation, 7 pages.

*Primary Examiner* — Michael Lebentritt
(74) *Attorney, Agent, or Firm* — Spano Law Group; Joseph S. Spano (57) ABSTRACT

Methods and systems for creating a measurement model based only on measured training data are presented. The trained measurement model is then used to calculate overlay values directly from measured scatterometry data. The measurement models receive scatterometry signals directly as input and provide overlay values as output. In some embodiments, overlay error is determined from measurements of design rule structures. In some other embodiments, overlay error is determined from measurements of specialized target structures. In a further aspect, the measurement model is trained and employed to measure additional parameters of interest, in addition to overlay, based on the same or different metrology targets. In some embodiments, measurement data from multiple targets, measurement data collected by multiple metrologies, or both, is used for model building, training, and measurement. In some embodiments, an opti- (Continued)

mization algorithm automates the measurement model building and training process.

20 Claims, 8 Drawing Sheets

(56) References Cited

U.S. PATENT DOCUMENTS

| | | | |
|---|---|---|---|
| 6,023,338 A | 2/2000 | Bareket | |
| 6,429,943 B1 | 8/2002 | Opsal et al. | |
| 6,716,646 B1 | 4/2004 | Wright et al. | |
| 6,778,275 B2 | 8/2004 | Bowes | |
| 6,787,773 B1 | 9/2004 | Lee | |
| 6,980,873 B2* | 12/2005 | Shen | G05B 23/024 |
| | | | 700/108 |
| 6,992,764 B1 | 1/2006 | Yang et al. | |
| 7,242,477 B2 | 7/2007 | Mieher et al. | |
| 7,283,237 B2* | 10/2007 | Sezginer | G01B 11/0616 |
| | | | 356/401 |
| 7,321,426 B1 | 1/2008 | Poslavsky et al. | |
| 7,478,019 B2 | 1/2009 | Zangooie et al. | |
| 7,616,313 B2 | 10/2009 | Kandel et al. | |
| 7,626,702 B2 | 12/2009 | Ausschnitt et al. | |
| 7,656,528 B2 | 2/2010 | Abdulhalim et al. | |
| 7,716,003 B1* | 5/2010 | Wack | G01N 21/4788 |
| | | | 356/625 |
| 7,826,072 B1* | 11/2010 | Wack | G01B 11/0625 |
| | | | 356/445 |
| 7,842,933 B2 | 11/2010 | Shur et al. | |
| 7,873,585 B2 | 1/2011 | Izikson | |
| 7,933,016 B2 | 4/2011 | Mieher et al. | |
| 7,933,026 B2 | 4/2011 | Opsal et al. | |
| 8,068,662 B2 | 11/2011 | Zhang et al. | |
| 8,138,498 B2 | 3/2012 | Ghinovker | |
| 8,525,994 B2 | 9/2013 | Abdulhalim et al. | |
| 8,570,515 B2 | 10/2013 | Abdulhalim et al. | |
| 9,347,872 B1* | 5/2016 | Poslavsky | G01N 21/211 |
| 9,915,522 B1 | 3/2018 | Jiang et al. | |
| 2003/0021465 A1 | 1/2003 | Adel et al. | |
| 2003/0224261 A1* | 12/2003 | Schulz | G01B 11/272 |
| | | | 430/22 |
| 2004/0233441 A1 | 11/2004 | Mieher et al. | |
| 2004/0267397 A1* | 12/2004 | Doddi | G01B 11/24 |
| | | | 700/110 |
| 2007/0221842 A1 | 9/2007 | Morokuma et al. | |
| 2008/0117434 A1* | 5/2008 | Verstappen | G01B 11/24 |
| | | | 356/521 |
| 2008/0281545 A1 | 11/2008 | McIntyre et al. | |
| 2009/0063378 A1 | 3/2009 | Izikson | |
| 2009/0152463 A1 | 6/2009 | Toyoda et al. | |
| 2009/0259605 A1* | 10/2009 | Opsal | G01B 11/0641 |
| | | | 706/15 |
| 2009/0291513 A1 | 11/2009 | Ghinovker et al. | |
| 2011/0266440 A1 | 11/2011 | Boughorbel et al. | |
| 2011/0307424 A1 | 12/2011 | Jin et al. | |
| 2012/0199287 A1 | 8/2012 | Vuong et al. | |
| 2012/0292502 A1 | 11/2012 | Langer et al. | |
| 2013/0208279 A1 | 8/2013 | Smith | |
| 2013/0259358 A1 | 10/2013 | Chen et al. | |
| 2013/0304408 A1* | 11/2013 | Pandev | H01L 22/20 |
| | | | 702/83 |
| 2014/0172394 A1 | 6/2014 | Kuznetsov et al. | |
| 2014/0222380 A1 | 8/2014 | Kuznetsov et al. | |
| 2014/0297211 A1* | 10/2014 | Pandev | G03F 7/70558 |
| | | | 702/81 |
| 2014/0316730 A1* | 10/2014 | Shchegrov | H01L 22/12 |
| | | | 702/81 |
| 2014/0375983 A1* | 12/2014 | Wolf | G01B 11/0625 |
| | | | 356/72 |
| 2015/0042984 A1 | 2/2015 | Pandev | |
| 2015/0046118 A1* | 2/2015 | Pandev | H01L 22/12 |
| | | | 702/155 |
| 2015/0117610 A1 | 4/2015 | Veldman et al. | |
| 2015/0176985 A1* | 6/2015 | Shchegrov | H01L 22/12 |
| | | | 356/614 |
| 2016/0117812 A1* | 4/2016 | Pandev | G06T 7/0004 |
| | | | 382/149 |
| 2016/0117847 A1* | 4/2016 | Pandev | G06T 7/001 |
| | | | 348/87 |
| 2016/0282105 A1* | 9/2016 | Pandev | G01B 11/0616 |

* cited by examiner

|  | POLY-MCD | POLY-HT | OXIDE-T | NITRIDE-T | BARC-T | RESIST-MCD | RESIST-HT | G3-SWA-R | G5-SWA-R |
|---|---|---|---|---|---|---|---|---|---|
| POLY-MCD | 0.03 | 0.11 | 0.14 | 0.19 | 0.10 | 0.13 | 0.14 | 0.08 | 0.07 |
| POLY-HT | | 0.71 | 0.45 | 0.41 | 0.36 | 0.35 | 0.34 | 0.33 | 0.08 |
| OXIDE-T | | | 0.42 | 0.40 | 0.10 | 0.10 | 0.08 | 0.04 | 0.03 |
| NITRIDE-T | | | | 0.97 | 0.58 | 0.52 | 0.46 | 0.22 | 0.14 |
| BARC-T | | | | | 0.61 | 0.55 | 0.47 | 0.20 | 0.11 |
| RESIST-MCD | | | | | | 0.92 | 0.82 | 0.41 | 0.13 |
| RESIST-HT | | | | | | | 0.93 | 0.40 | 0.31 |
| G3-SWA-R | | | | | | | | 0.36 | 0.50 |
| G5-SWA-R | | | | | | | | | 0.05 |

FIG. 11

SIGNAL RESPONSE METROLOGY FOR SCATTEROMETRY BASED OVERLAY MEASUREMENTS

CROSS REFERENCE TO RELATED APPLICATION

The present application for patent claims priority under 35 U.S.C. § 119 from U.S. provisional patent application Ser. No. 61/991,395, entitled "Method and Metrology Targets for Measuring Overlay and Other Semiconductor Device or Process Parameters," filed May 9, 2014, the subject matter of which is incorporated herein by reference in its entirety.

TECHNICAL FIELD

The described embodiments relate to metrology systems and methods, and more particularly to methods and systems for improved overlay measurement.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

Semiconductor devices are often fabricated by depositing a series of layers on a substrate. Some or all of the layers include various patterned structures. The relative position of structures both within particular layers and between layers is critical to the performance of completed electronic devices. Overlay refers to the relative position of overlying or interlaced structures on the same or different layers of a wafer. Overlay error refers to deviations from the nominal (i.e., desired) relative position of overlying or interlaced structures. The greater the overlay error, the more the structures are misaligned. If the overlay error is too great, the performance of the manufactured electronic device may be compromised.

Scatterometry overlay (SCOL) metrology techniques have been applied to the characterization of overlay errors. These methods are based primarily on differential measurements of optical signals corresponding to diffraction from two different targets each with programmed overlay offsets. The unknown overlay error is extracted based on these differential measurements.

In most existing methods, overlay error is characterized based on a metric sensitive to asymmetry of the structure. For example, existing angle-resolved scatterometry overlay (SCOL) involves a characterization of the asymmetry between the +1 and −1 diffracted orders that is indicative of overlay error. However, relying on asymmetry as the indicator of overlay error is problematic because other asymmetries such as line profile asymmetry or beam illumination asymmetry couple into the overlay-generated asymmetry in the measurement signal. This results in an inaccurate measurement of overlay error.

In existing methods, overlay error is typically evaluated based on measurements of specialized target structures formed at various locations on the wafer by a lithography tool. The target structures may take many forms, such as a box in box structure. In this form, a box is created on one layer of the wafer and a second, smaller box is created on another layer. The localized overlay error is measured by comparing the alignment between the centers of the two boxes. Such measurements are taken at locations on the wafer where target structures are available.

Unfortunately, these specialized target structures often do not conform to the design rules of the particular semiconductor manufacturing process being employed to generate the electronic device. This leads to errors in estimation of overlay errors associated with actual device structures that are manufactured in accordance with the applicable design rules. For example, image-based overlay metrology often requires the pattern to be resolved with an optical microscope that requires thick lines with critical dimensions far exceeding design rule critical dimensions. In another example, angle-resolved SCOL often requires large pitch targets to generate sufficient signal at the +1 and −1 propagating diffraction orders from the overlay targets. In some examples, pitch values in the range 500-800 nm may be used. Meanwhile, actual device pitches for logic or memory applications (design rule dimensions) may be much smaller, e.g., in the range 100-400 nm, or even below 100 nm.

Future overlay metrology applications present challenges for metrology due to increasingly small resolution requirements and the increasingly high value of wafer area. Thus, methods and systems for improved overlay measurements are desired.

SUMMARY

Methods and systems for measuring overlay error between structures formed on a substrate by successive lithographic processes are presented herein. Overlay error is directly measured based on a measurement model created from raw scatterometry data. The measurement model is trained based on measurements of sites with known overlay variations. The measurement model is then used to predict the overlay errors from a measurement site having unknown overlay error.

In a further aspect, signal response metrology (SRM) is employed to measure additional parameters of interest (e.g., focus/dose, critical dimensions, etc.), in addition to overlay, from the same or different metrology targets. In these examples, the measured, scatterometry-based training data also includes known values of the parameters of interest. In this manner, the trained measurement model is sensitive to these parameters of interest, in addition to overlay.

In a further aspect, the metrology targets are preferably design rule targets. In other words, the metrology targets adhere to the design rules applicable to the underlying semiconductor manufacturing process. In some examples, the metrology targets are located within the active die area. In other examples, the design rule targets are located in the scribe line area. In some examples, the metrology targets have dimensions of 15 μm by 15 μm, or smaller. In this manner, the impact on overlay of intra-field variations induced by lithographic imperfections can be analyzed.

By using only raw scatterometry data to create the measurement model, as described herein, the errors and approximations associated with traditional model based metrology methods are reduced. In addition, the measurement model is not sensitive to systematic errors, asymmetries, etc. because the measurement model is trained based on scatterometry data collected from a particular metrology system and used to perform measurements based on scatterometry data collected from the same metrology system.

The trained, scatterometry-based measurement models described herein receive scatterometry data directly as input and provide values of overlay error as output. By streamlining the measurement process, the predictive results are improved along with a reduction in computation and user time.

In another further aspect, the metrology system employed to perform overlay measurements as described herein includes an infrared optical measurement system. The infrared illumination light penetrates opaque structures disposed between layers of patterned structures employed to evaluate overlay.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for measuring overlay error between structures formed on a substrate by successive lithographic processes is directly measured based on a measurement model created from raw scatterometry data as described herein. The measurement model is trained based on measurements of sites with known overlay variations. The measurement model is then used to predict the overlay errors from a measurement site having unknown overlay error. In general, the measured structures may be located on the same layer or on different layers of the substrate.

In a further aspect, the signal response metrology (SRM) is employed to measure additional parameters of interest (e.g., focus/dose, critical dimensions, etc.), in addition to overlay, from the same or different metrology targets. In these examples, the measured, scatterometry-based training data also includes known values of the parameters of interest. In this manner, the trained measurement model is sensitive to these parameters of interest. Such a trained measurement model is employed to characterize both overlay and other parameters of interest.

In a further aspect, the metrology targets located on one or more measurement sites of a DOE wafer are preferably design rule targets. In other words, the metrology targets adhere to the design rules applicable to the underlying semiconductor manufacturing process. In some examples, the metrology targets are preferably located within the active die area. In some examples, the metrology targets have dimensions of 15 μm by 15 μm, or smaller. In this manner, the impact on overlay of intra-field variations induced by lithographic imperfections can be analyzed.

In some examples, the metrology targets are on-device structures. Scatterometry data collected from on-device structures are used to train a measurement model as described herein. The trained measurement model is then used to calculate values of overlay, and, in some examples, one or more parameters of interest directly from scatterometry data collected from the same on-device structures fabricated on other wafers. In these examples, the use of specialized targets is avoided.

By using only raw scatterometry data to create the measurement model, as described herein, the errors and approximations associated with traditional model based metrology methods are reduced. In addition, the measurement model is not sensitive to systematic errors, asymmetries, etc. because the measurement model is trained based on scatterometry data collected from a particular metrology system and used to perform measurements based on scatterometry data collected from the same metrology system.

The trained, scatterometry-based measurement models described herein receive scatterometry data directly as input and provide values of overlay error as output. By streamlining the measurement process, the predictive results are improved along with a reduction in computation and user time. In some examples, the measurement model can be created in less than an hour. In addition, by employing a simplified model, measurement time is reduced compared to existing metrology methods.

Figure 1:
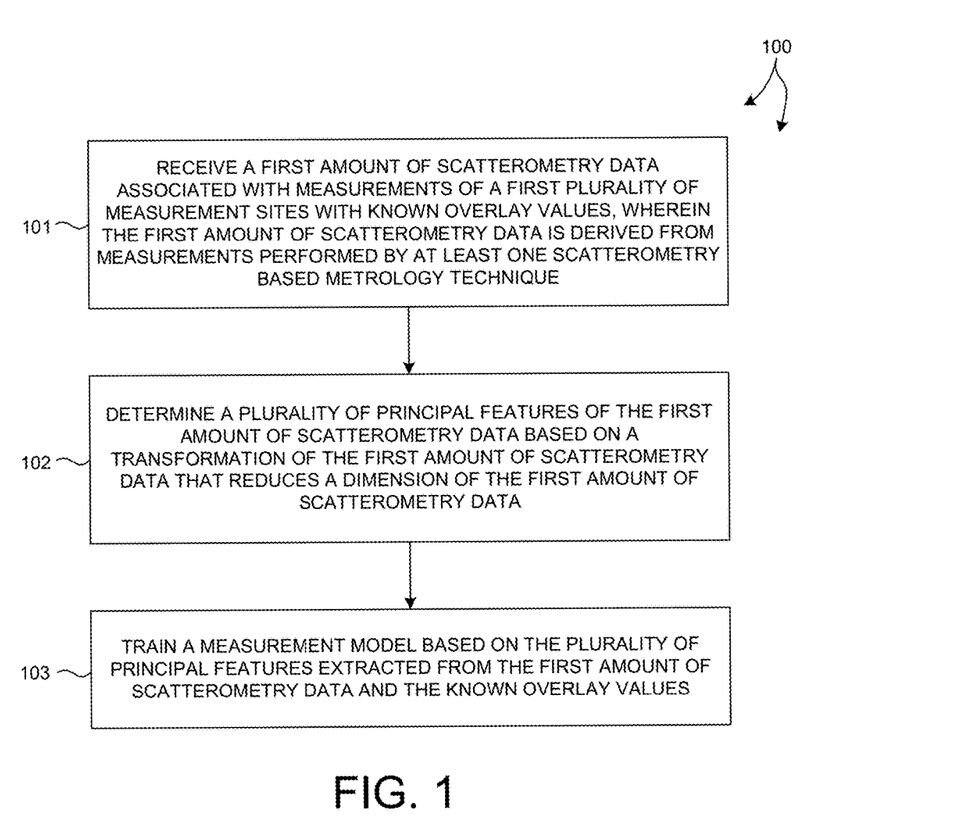
FIG. 1 is a flowchart illustrative of a method 100 of training a signal response metrology (SRM) measurement model as described herein.
Figure 3:
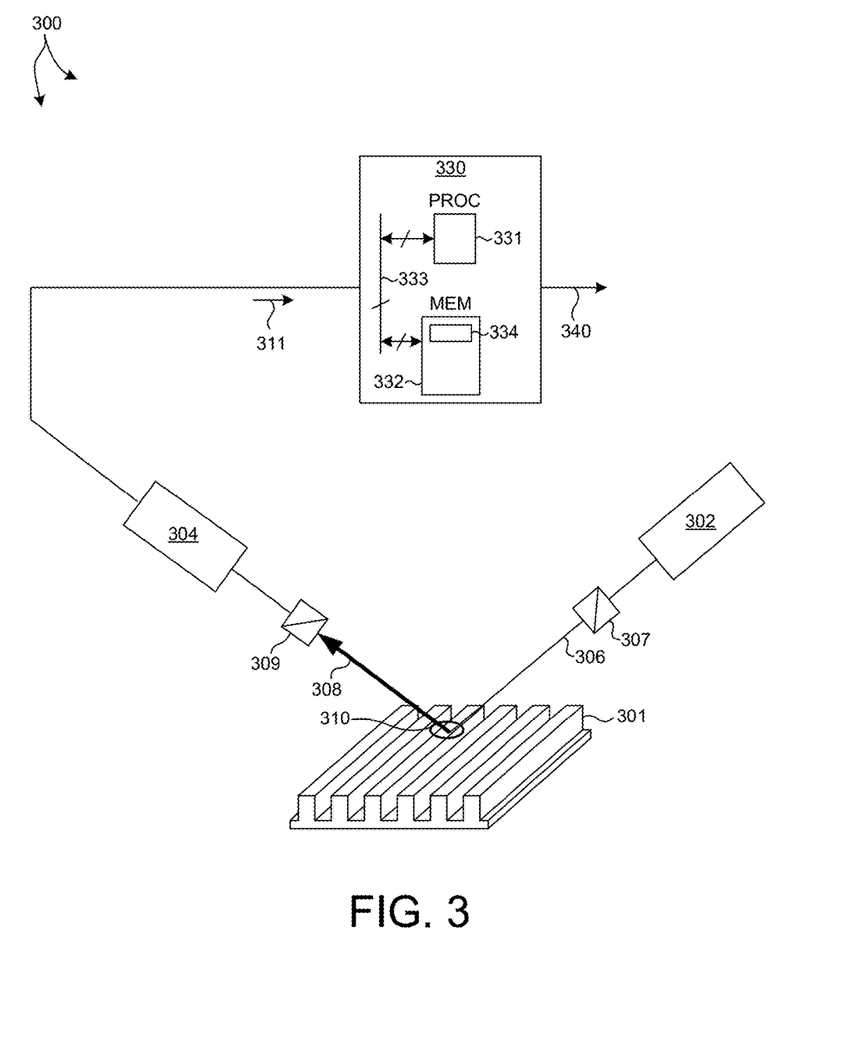
FIG. 3 illustrates a system 300 for estimating overlay from signals collected from a specimen in accordance with the exemplary methods presented herein.

FIG. 1 illustrates a method 100 suitable for implementation by a metrology system such as metrology system 300 illustrated in FIG. 3 of the present invention. In one aspect, it is recognized that data processing blocks of method 100 may be carried out via a pre-programmed algorithm executed by one or more processors of computing system 330, or any other general purpose computing system. It is recognized herein that the particular structural aspects of metrology system 300 do not represent limitations and should be interpreted as illustrative only.

In block 101, a first amount of scatterometry data associated with measurements of a first plurality of measurement sites is received by a computing system (e.g., computing system 330). The measurement sites include known variations in overlay. The scatterometry data is derived from measurements performed by at least one scatterometry based metrology technique. The measurement data can be obtained from an optical scatterometry system, an x-ray scatterometry system, or other scatterometry based measurement system. In some examples, optical measurements are performed, for example, with a spectroscopic ellipsometry (SE) tool that provides a broad range of wavelengths and also information about phase delay between two independent polarizations. In some examples, Mueller matrix SE may also be employed. In some other examples, optical measurements are performed by a wavelength-resolved or angle-resolved reflectometer.

Figure 7:
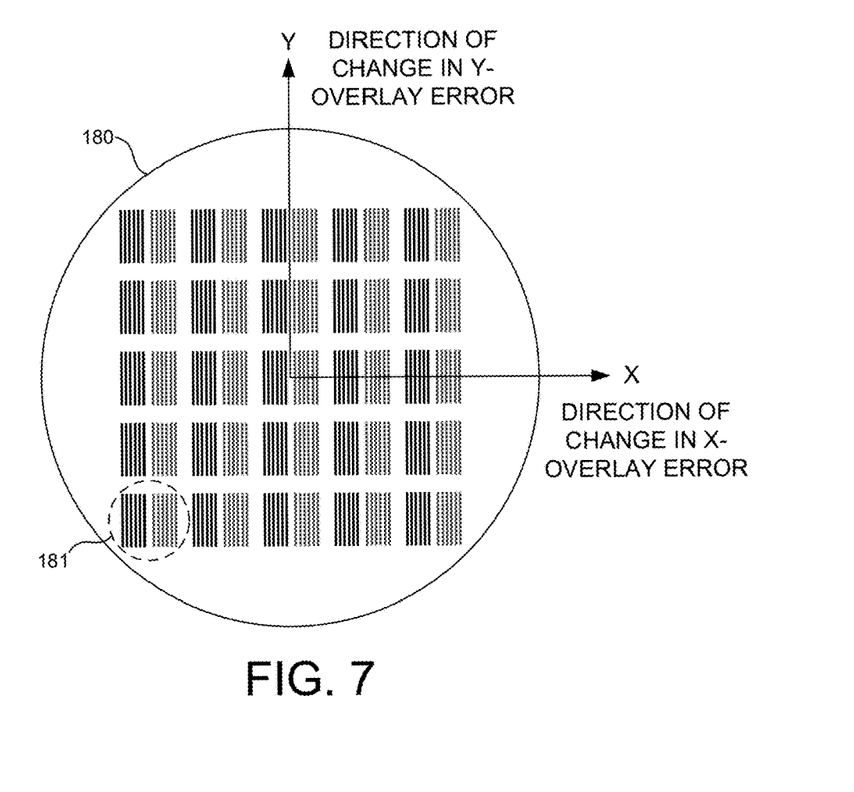
FIG. 7 illustrates a DOE wafer 180 having a grid of targets that exhibit known variations in overlay error in one embodiment.

In some embodiments, variations of overlay are organized in a Design of Experiments (DOE) pattern on the surface of a semiconductor wafer (e.g., DOE wafer). In this manner, the measurement sites interrogate different locations on the wafer surface that correspond with different overlay values. In one example, the DOE pattern is an overlay error pattern. Typically, a DOE wafer exhibiting an overlay error pattern includes a grid pattern of measurement sites. In one grid direction (e.g., the x-direction), the overlay is varied in the x-direction while the overlay in the y-direction is held constant. In the orthogonal grid direction (e.g., the y-direction), the overlay error in the y-direction is varied while the overlay error in the x-direction is held constant. In this manner, scatterometry data collected from the DOE wafer includes data associated with known variations in the overlay in both the x and y directions. FIG. 7 depicts a DOE wafer 180 having a grid of targets (e.g., target 181) that exhibit known variations in overlay error. The x-direction overlay errors vary as a function of location on the DOE wafer 180 in the x-direction. The y-direction overlay errors vary as a function of location on the DOE wafer 180 in the y-direction. In some examples, the x and y overlay errors range from −20 nanometers to 20 nanometers. In some other examples, the x and y overlay errors range from −80 to 80 nanometers.

Figure 4:
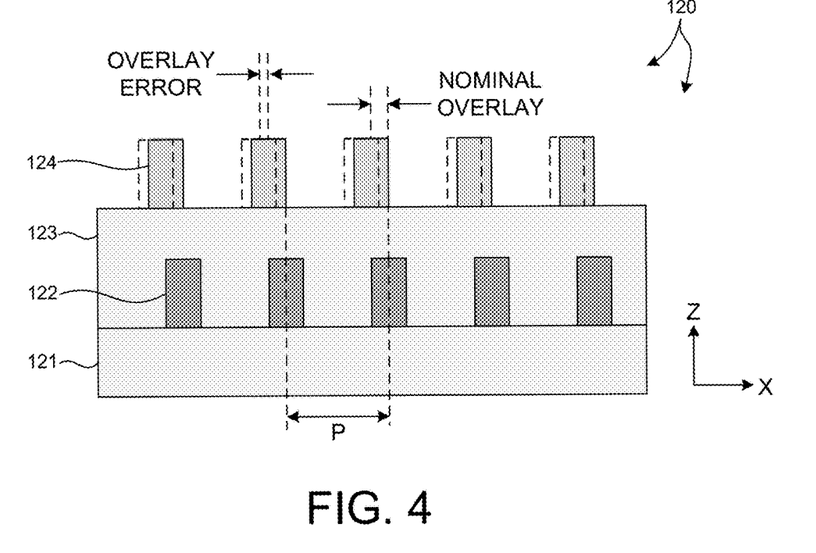
FIG. 4 illustrates a multi-layer, line/space metrology target 120.

FIG. 4 depicts a multi-layer metrology target 120 that includes a substrate 121, a grating structure 122, a fill layer 123, and another grating structure 124 that is spatially offset in the x-direction from the first patterned structure 122. The pitch of both patterned structures 122 and 124 is a distance, P. In most cases, sensitivity to overlay error is at its minimum when there is no overlay. In the depicted embodiment, the patterned structure 124 is offset from patterned structure 122 by a nominal overlay offset to increase measurement sensitivity. In some embodiments, a series of overlay training targets is provided each having a different of overlay error. In the embodiment depicted in FIG. 4, overlay error is the displacement of the patterned structure 124 relative to its nominal overlay offset. In some embodiments, a range of overlay errors is centered about a nominal overlay value. In one example, a series of overlay training targets includes a nominal overlay of P/4 within a range of overlay positions from P/8 to 3P/8.

A variety of different metrology targets may be contemplated within the scope of this invention. In some embodiments, the metrology targets are based on conventional line/space targets. In some other embodiments, the metrology targets are device-like structures. In some other embodiments, the metrology targets are the actual devices themselves, thus no specialized metrology target is employed. Regardless of the type of metrology target employed, a set of training targets having programmed (known) offsets must be provided to train the measurement model. Once the model is trained, it may be used to perform measurements of structures having unknown overlay.

The training targets may be provided on a separate training wafer or on a production wafer. In some examples, the metrology targets are located in a scribeline of a production wafer. In some other examples, the metrology targets are located in the active die area.

In some embodiments, the measurements used for model training are performed in a scribeline area and subsequent measurements are performed in a periodic area of the actual device, e.g., in a 10 mm by 10 mm area using small spot SE.

Figure 5:
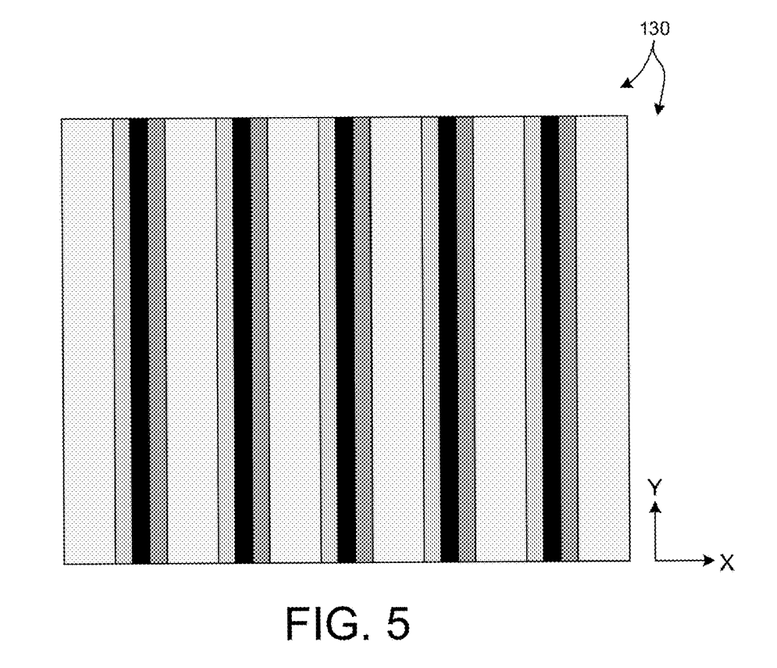
FIG. 5 illustrates a multi-layer, line/space metrology target 130 having two grating structures offset in the x-direction.
Figure 6:
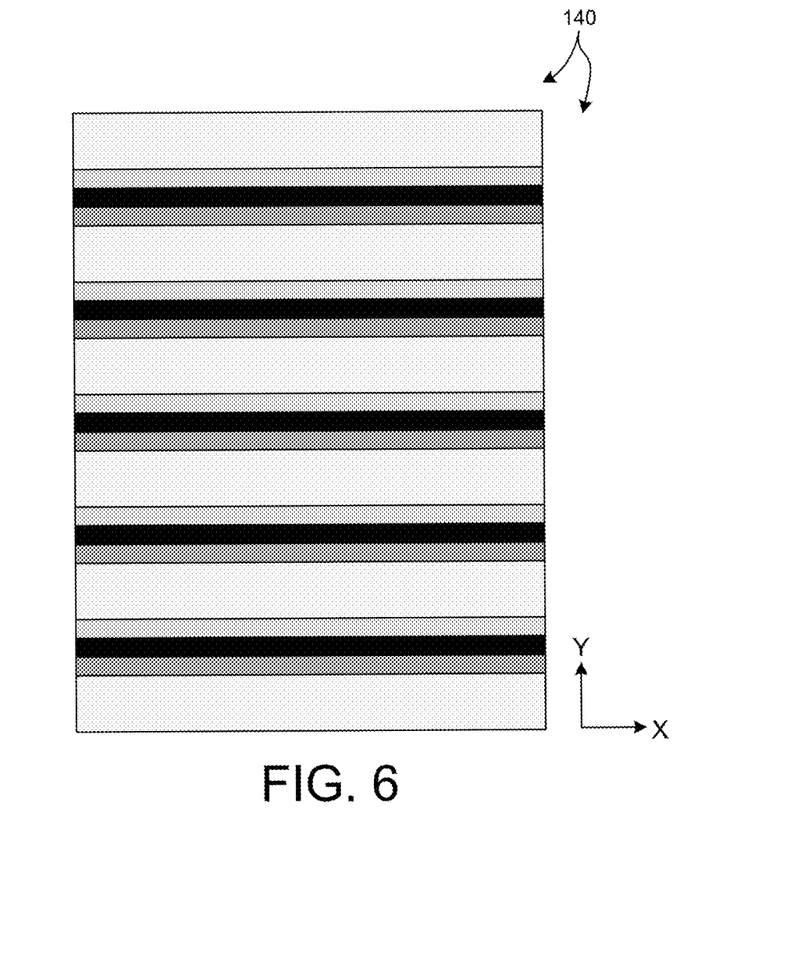
FIG. 6 illustrates a multi-layer, line/space metrology target 140 having two grating structures offset in the y-direction.

In some embodiments, grating targets are provided that have offset patterns in both the x and y directions. For example, FIG. 5 depicts a metrology target 130 having two offset grating structures as described with reference to FIG. 4. In the embodiment depicted in FIG. 5, the grating structures are offset in the x-direction. FIG. 6 depicts a metrology target 140 having two offset grating structures as described with reference to FIG. 4. In the embodiment depicted in FIG. 6, the grating structures are offset in the y-direction.

In some embodiments, multiple, different targets offset in orthogonal directions are employed in each die. This may be advantageous to minimize the effects of underlayers on measurement accuracy.

As described hereinbefore, the measurement methods and systems described herein are not constrained to specialized targets. In general, any target that exhibits sensitivity to overlay when measured by the available measurement system may be employed in accordance with the methods and systems described herein.

In block 102, a number of principal features are extracted from the scatterometry training data based on a mathematical transformation. The transformation reduces the dimension of the scatterometry data and maps the original signals to a new reduced set of signals. The transformation is determined based on the variations in overlay in the scatterometry training data. Each measured signal is treated as an original signal that changes within the process range for different overlay measurements in the set of scatterometry training data. The transformation may be applied to all of measurement signals, or a subset of measurement signals. In some examples, the signals subject to analysis are chosen randomly. In some other examples, the signals subject to analysis are chosen due to their relatively high sensitivity to changes in overlay. For example, signals that are not sensitive to changes in overlay may be ignored.

By way of non-limiting example, the transformation may be achieved using any of a principal component analysis (PCA) model, a kernel PCA model, a non-linear PCA model, an independent component analysis (ICA) model or other dimensionality reduction methods using dictionaries, a discrete cosine transform (DCT) model, fast fourier transform (FFT) model, a wavelet model, etc.

One or more features are extracted from the scatterometry training data. In some examples, the training data is analyzed using Principal Components Analysis (PCA), or non-linear PCA, to extract features that most strongly reflect the variations in overlay that are present at the different measurement sites. In some examples, individual signals that most strongly reflect overlay variation present at the different measurement sites may be selected from multiple signals present in the training data.

In block 103, a measurement model is trained based on the principal features extracted from the scatterometry training data and the known overlay values. The measurement model is structured to receive measurement data generated by a metrology system at one or more measurement sites, and directly determine the overlay associated with each measurement target. In some embodiments, the measurement model is implemented as a neural network model. In one example, the number of nodes of the neural network is selected based on the features extracted from the training data. In other examples, the measurement model may be implemented as a linear model, a polynomial model, a response surface model, a support vector machines model, or other types of models. In some examples, the measurement model may be implemented as a combination of models. The selected model is trained based on the principal features (reduced set of signals) and the known variations in overlay. The model is trained such that its output fits the defined variations in overlay for all the measured signals in the overlay variation space defined by the set of DOE metrology targets.

Figure 2:
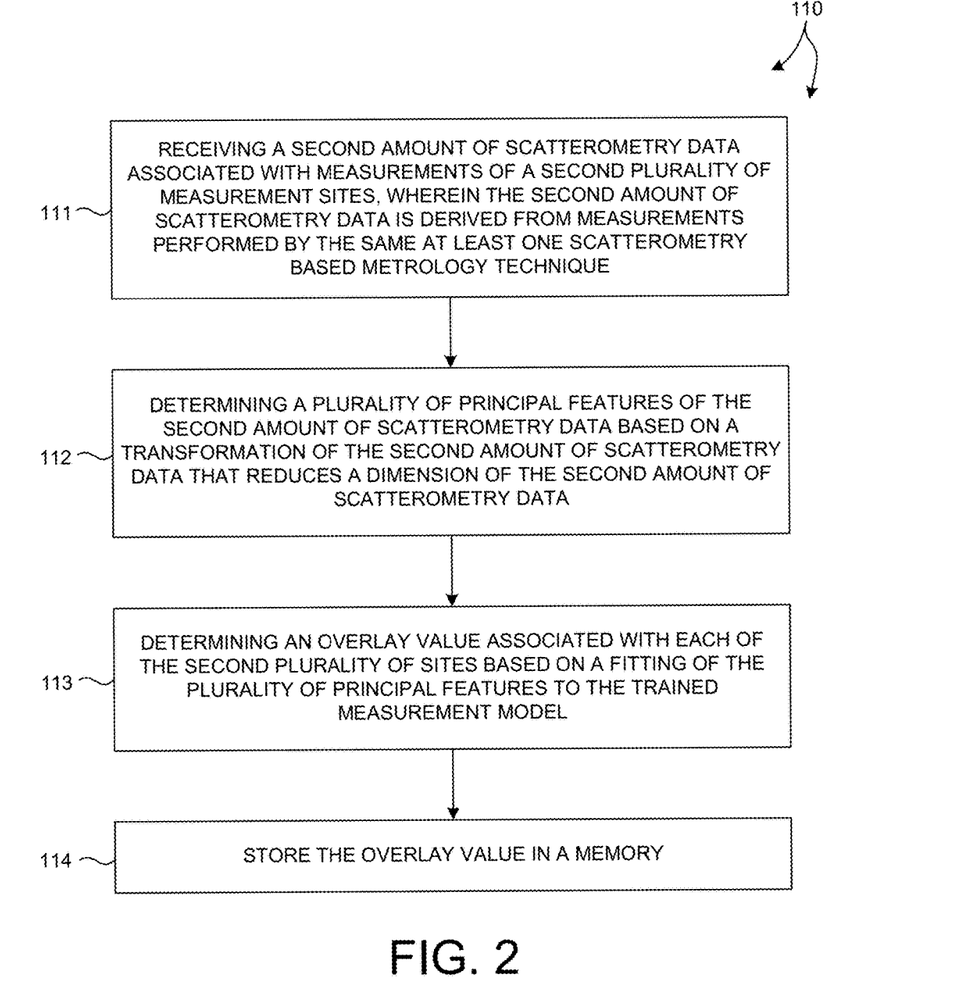
FIG. 2 is a flowchart illustrative of a method 110 of measuring overlay using a trained measurement model generated by method 100.

In another aspect, the trained model is employed as the measurement model for measurement of other targets having unknown overlay values. FIG. 2 illustrates a method 110 suitable for implementation by a metrology system such as metrology system 300 illustrated in FIG. 3 of the present invention. In one aspect, it is recognized that data processing blocks of method 110 may be carried out via a pre-programmed algorithm executed by one or more processors of computing system 330, or any other general purpose computing system. It is recognized herein that the particular structural aspects of metrology system 300 do not represent limitations and should be interpreted as illustrative only.

In block 111, an amount of scatterometry data associated with measurements of a plurality of measurement sites is received by a computing system (e.g., computing system 330). The scatterometry data is derived from measurements performed by the same metrology technique, or combination of metrology techniques as described with reference to method 100. Similarly, the scatterometry data includes measurements of the same types of structures as described with reference to method 100, but with unknown overlay errors.

In block 112, principal features from at least a portion of the measured data are determined based on a mathematical transformation that reduces the dimension of the measured data. In some embodiments, the transformation is the same transformation employed to reduce the dimension of the corresponding training data described with reference to method 100. It is preferred to extract features from the scatterometry data using the same analysis employed to extract features from the training data in method 100. In this manner, the dimension reduction of the acquired data is performed by the same transformation used to reduce the dimension of the training data.

In block 113, the overlay value associated with each of the plurality of sites is determined based on a fitting of the determined principal features to a trained measurement model (e.g., the trained measurement model described with reference to method 100). In this manner, overlay is determined based on the trained measurement model and the reduced set of measurement signals.

In block 114, the determined overlay value(s) are stored in a memory. For example, the overlay values may be stored on-board the measurement system 300, for example, in memory 332, or may be communicated (e.g., via output signal 340) to an external memory device.

In some examples, the measurement performance of the trained measurement model is determined by using the model to measure a set of metrology targets that have not participated as part of the training data set, but have known overlay error. The differences between the expected and measured overlay are indicative of model performance.

In a further aspect, the methods and systems described herein are not limited only to the measurement of overlay errors. In general, the aforementioned scatterometry-based measurement techniques may be applied to the measurement of other process, structure, dispersion parameters, or any combination of these parameters. By way of non-limiting example, profile geometry parameters (e.g., critical dimension), process parameters (e.g., focus, and dose), dispersion parameters, pitch walk, or any combination of parameters may be measured along with overlay error using the aforementioned techniques. A set of training targets with programmed variations for each parameter of interest must be provided. The measurement model is then trained based on scatterometry data collected over measurement sites that include the range of programmed variations of each parameter of interest as described herein with reference to overlay.

In another further aspect, the methods and systems for training the measurement model include an optimization algorithm to automate any or all of the elements required to arrive at a trained measurement model.

In some examples, an optimization algorithm is configured to maximize the performance of the measurement (defined by a cost function) by optimizing any or all of the following parameters: the type of feature extraction model (i.e., transformation), the parameters of the selected feature extraction model, the type of measurement model, the parameters of the selected measurement model. The optimization algorithm can include user defined heuristics and can be combination of nested optimizations (e.g., combinatorial and continuous optimization).

In a further aspect, scatterometry data from multiple, different targets is collected for model building, training, and measurement. The use of data associated with multiple targets having different structure, but formed by the same process conditions increases the information embedded in the model and reduces the overlay correlation to process or other parameter variations. The additional information embedded in the model allows for a decoupling of information content associated with overlay from information associated with other parameters (e.g., film thicknesses, CD, etc.) that may affect the measured signals in a similar manner. In these examples, the use of training data that includes images of multiple, different targets at one or more measurement sites enables more accurate overlay estimation. In some examples, a mixture of isolated and dense line/space targets is employed to decouple overlay from underlayer effects.

In another further aspect, signals from multiple targets can be processed to reduce sensitivity to process variations and increase sensitivity to the parameters of interest. In some examples, signals from different targets are subtracted from one another. In some other examples, signals from different targets are fit to a model, and the residuals are used to build, train, and use the measurement model as described herein. In one example, signals from two different targets are subtracted to eliminate, or significantly reduce, the effect of process noise in each measurement result. In general, various mathematical operations can be applied between the signals from different targets to determine signals with reduced sensitivity to process variations and increased sensitivity to the parameters of interest.

In another further aspect, measurement data derived from measurements performed by a combination of multiple, different measurement techniques is collected for model building, training, and measurement. The use of measurement data associated with multiple, different measurement techniques increases the information content in the combined set of signals and reduces the overlay correlation to process or other parameters variations. Measurement data may be derived from measurements performed by any combination of multiple, different measurement techniques. In this manner, different measurement sites may be measured by multiple, different measurement techniques (e.g., optical SE, SAXS, etc.) to enhance the measurement information available for estimation of parameters of interest.

In general, any measurement technique, or combination of two or more measurement techniques may be contemplated within the scope of this patent document as the data processed by the feature extraction model and the measurement model for training and measurement is in vector form. Because the signal response metrology techniques as described herein operate on vectors of data, each collected signal is treated independently. In addition, it is possible to concatenate data from multiple, different metrologies, regardless of whether the data is two dimensional data, one dimensional data, or even single point data.

Exemplary measurement techniques that may provide data for analysis in accordance with the signal response metrology techniques described herein include, but are not limited to spectroscopic ellipsometry, including Mueller matrix ellipsometry, spectroscopic reflectometry, spectroscopic scatterometry, scatterometry overlay, beam profile reflectometry, both angle-resolved and polarization-resolved, beam profile ellipsometry, single or multiple discrete wavelength ellipsometry, transmission small angle x-ray scatterometer (TSAXS), small angle x-ray scattering (SAXS), grazing incidence small angle x-ray scattering (GISAXS), wide angle x-ray scattering (WAXS), x-ray reflectivity (XRR), x-ray diffraction (XRD), grazing incidence x-ray diffraction (GIXRD), high resolution x-ray diffraction (HRXRD), x-ray photoelectron spectroscopy (XPS), x-ray fluorescence (XRF), grazing incidence x-ray fluorescence (GIXRF), x-ray tomography, and x-ray ellipsometry. In general, any metrology technique applicable to the characterization of semiconductor structures, including image based metrology techniques, may be contemplated, individually, or in any combination.

In another further aspect, signals measured by multiple metrologies can be processed to reduce sensitivity to process variations and increase sensitivity to the parameters of interest. In some examples, signals from targets measured by different metrologies are subtracted from one another. In some other examples, signals from targets measured by different metrologies are fit to a model, and the residuals are used to build, train, and use the measurement model as described herein. In one example, signals from a target measured by two different metrologies are subtracted to eliminate, or significantly reduce, the effect of process noise in each measurement result. In general, various mathematical operations can be applied between the signals measured by different metrologies to determine signals with reduced sensitivity to process variations and increased sensitivity to the parameters of interest.

In general, signals from multiple targets each measured by multiple metrology techniques increases the information content in the combined set of signals and reduces the overlay correlation to process or other parameters variations.

FIG. 3 illustrates a system 300 for measuring characteristics of a specimen in accordance with the exemplary methods presented herein. As shown in FIG. 3, the system 300 may be used to perform spectroscopic ellipsometry measurements of one or more structures of a specimen 301. In this aspect, the system 300 may include a spectroscopic ellipsometer equipped with an illuminator 302 and a spectrometer 304. The illuminator 302 of the system 300 is configured to generate and direct illumination of a selected wavelength range (e.g., 100-2500 nm) to the structure disposed on the surface of the specimen 301. In turn, the spectrometer 304 is configured to receive illumination reflected from the surface of the specimen 301. It is further noted that the light emerging from the illuminator 302 is polarized using a polarization state generator 307 to produce a polarized illumination beam 306. The radiation reflected by the structure disposed on the specimen 301 is passed through a polarization state analyzer 309 and to the spectrometer 304. The radiation received by the spectrometer 304 in the collection beam 308 is analyzed with regard to polarization state, allowing for spectral analysis by the spectrometer of radiation passed by the analyzer. These spectra 311 are passed to the computing system 330 for analysis of the structure.

As depicted in FIG. 3, system 300 includes a single measurement technology (i.e., SE). However, in general, system 300 may include any number of different measurement technologies. By way of non-limiting example, system 300 may be configured as a spectroscopic ellipsometer (including Mueller matrix ellipsometry), a spectroscopic reflectometer, a spectroscopic scatterometer, an overlay scatterometer, an angular resolved beam profile reflectometer, a polarization resolved beam profile reflectometer, a beam profile reflectometer, a beam profile ellipsometer, any single or multiple wavelength ellipsometer, or any combination thereof. Furthermore, in general, measurement data collected by different measurement technologies and analyzed in accordance with the methods described herein may be collected from multiple tools, rather than one tool integrating multiple technologies.

In a further embodiment, system 300 may include one or more computing systems 330 employed to perform overlay measurements based on measurement models developed in accordance with the methods described herein. The one or more computing systems 330 may be communicatively coupled to the spectrometer 304. In one aspect, the one or more computing systems 330 are configured to receive measurement data 311 associated with measurements of the structure of specimen 301.

It should be recognized that the various steps described throughout the present disclosure may be carried out by a single computer system 330 or, alternatively, a multiple computer system 330. Moreover, different subsystems of the system 300, such as the spectroscopic ellipsometer 304, may include a computer system suitable for carrying out at least a portion of the steps described herein. Therefore, the aforementioned description should not be interpreted as a limitation on the present invention but merely an illustration. Further, the one or more computing systems 330 may be configured to perform any other step(s) of any of the method embodiments described herein.

In addition, the computer system 330 may be communicatively coupled to the spectrometer 304 in any manner known in the art. For example, the one or more computing systems 330 may be coupled to computing systems associated with the spectrometer 304. In another example, the spectrometer 304 may be controlled directly by a single computer system coupled to computer system 330.

The computer system 330 of the metrology system 300 may be configured to receive and/or acquire data or information from the subsystems of the system (e.g., spectrometer 304 and the like) by a transmission medium that may include wireline and/or wireless portions. In this manner, the transmission medium may serve as a data link between the computer system 330 and other subsystems of the system 300.

Computer system 330 of the integrated metrology system 300 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 330 and other systems (e.g., memory on-board metrology system 300, external memory, reference measurement source 320, or other external systems). For example, the computing system 330 may be configured to receive measurement data from a storage medium (i.e., memory 332 or an external memory) via a data link. For instance, spectral results obtained using spectrometer 304 may be stored in a permanent or semi-permanent memory device (e.g., memory 332 or an external memory). In this regard, the spectral results may be imported from on-board memory or from an external memory system. Moreover, the computer system 330 may send data to other systems via a transmission medium. For instance, an integrated measurement model or a specimen parameter 340 determined by computer system 330 may be communicated and stored in an external memory. In this regard, measurement results may be exported to another system.

Computing system 330 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 334 implementing methods such as those described herein may be transmitted over a transmission medium such as a wire, cable, or wireless transmission link. For example, as illustrated in FIG. 19, program instructions 334 stored in memory 332 are transmitted to processor 331 over bus 333. Program instructions 334 are stored in a computer readable medium (e.g., memory 332). Exemplary computer-readable media include read-only memory, a random access memory, a magnetic or optical disk, or a magnetic tape.

In some examples, the model building, training, and measurement methods described herein are implemented as an element of a SpectraShape® optical critical-dimension metrology system available from KLA-Tencor Corporation, Milpitas, Calif., USA. In this manner, the model is created and ready for use immediately after the DOE wafer spectra are collected by the system.

In some other examples, the model building and training methods described herein are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

Figure 8:
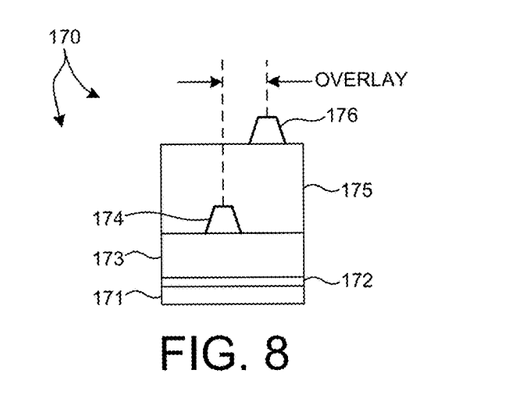
FIG. 8 illustrates a metrology target 170 measured by a rotating polarizer, rotating compensator (RPRC) SE measurement system as described with reference to FIG. 3.

FIG. 8 depicts a metrology target 170 measured by a rotating polarizer, rotating compensator (RPRC) SE measurement system as described with reference to FIG. 3. Metrology target 170 includes a substrate 171, a silicon oxide layer 172 that is 10 nanometers thick, and a silicon nitride layer 173 that is 55 nanometers thick. A polysilicon structure 174 having a middle critical dimension of 40 nanometers, a height of 55 nanometers, and a sidewall angle of 80 degrees is disposed on the silicon nitride layer 173. A bottom anti-reflective coating (BARC) 175 fills the layer that includes the polysilicon structure. A resist structure 176 is disposed on the BARC layer 175. The resist structure 176 also has a middle critical dimension of 40 nanometers, a height of 55 nanometers, and a sidewall angle of 80 degrees. The metrology target includes an overlay offset to be measured.

Figure 9:
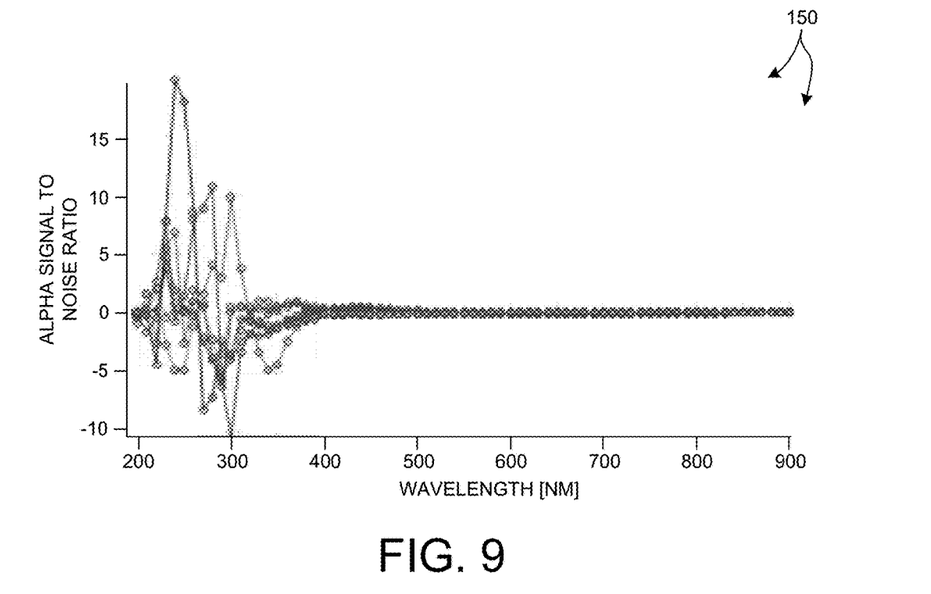
FIG. 9 illustrates a plot 150 of alpha values associated measurements of metrology target 170 by a RPRC SE system.
Figure 10:
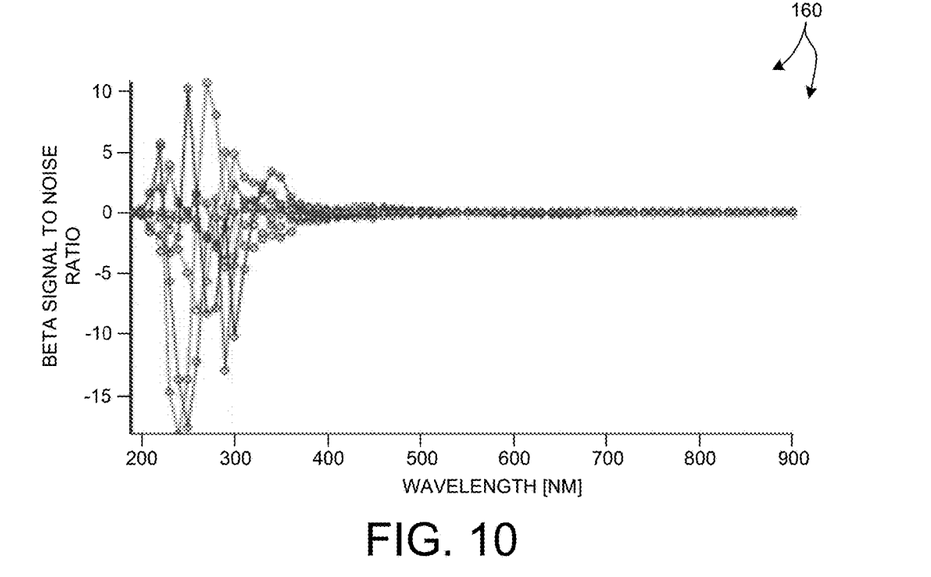
FIG. 10 illustrates a plot 160 of beta values associated measurements of metrology target 170 by a RPRC SE system.

Metrology target 170 was measured by a RPRC SE system having an angle of incidence of 65 degrees. Measurements were performed over a broad range of illumination wavelengths and for a number of different overlay values. FIG. 9 depicts a plot 150 of the measured alpha values over a range of wavelengths for each different overlay offset. FIG. 10 depicts a plot 160 of the measured beta values over the range of wavelengths for each different overlay offset. As depicted in FIGS. 9 and 10, the RPRC SE system is sensitive to overlay offset for illumination wavelengths below 400 nanometers.

Figure 11:
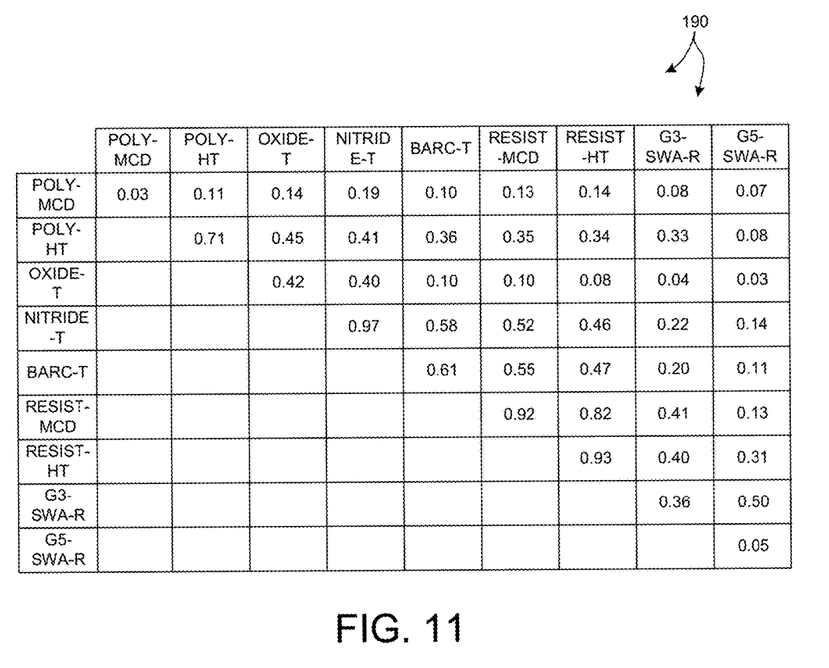
FIG. 11 depicts a table 190 of correlation values among different structural parameters of metrology target 170 derived from the measurements performed by the RPRC SE system.

FIG. 11 depicts a table 190 of correlation values among different structural parameters of metrology target 170 derived from measurements performed by the RPRC SE system at different values of overlay and other stack parameters such as line CD, height, layer thickness, and sidewall angle. In this example, the last two parameters depicted in table 190 correspond to the right sidewall angles (SWA-R) of the polysilicon and resist profiles. Their left sidewall angles are fixed. Thus, measurement performance in the face of asymmetry can be evaluated.

In a conventional differential target based scatterometry overlay analysis that relies on 1st order diffraction, the asymmetry of the profiles is highly correlated with the overlay parameter. This can lead to inaccuracy in overlay metrology. However, as illustrated in table 190, overlay shows low correlation with all parameters including asymmetry parameters for resist and polysilicon lines such as the right sidewall angle parameter. In this example, the low correlation of overlay with other parameters indicates that SRM can be performed and overlay measurements can be made with high reliability on design rule targets. In examples where correlation is unacceptably high, techniques such as multiple targets (e.g. iso and dense) and multiple metrology techniques may be employed as described herein.

The SRM methodology as described herein is applicable to many measurement techniques, or combinations of techniques that are sensitivity to overlay. Although 1st order angle-resolved scatterometry overlay may be employed, it is not preferred as it requires targets having relatively large pitch and can lead to inaccuracies.

In another further aspect, the metrology system employed to perform overlay measurements as described herein (e.g., metrology system 300) includes an infrared optical measurement system. In these embodiments, the metrology system 300 an infrared light source (e.g., an arc lamp, an electrode-less lamp, a laser sustained plasma (LSP) source, or a supercontinuum source). An infrared supercontinuum laser source is preferred over a traditional lamp source because of the higher achievable power and brightness in the infrared region of the light spectrum. In some examples, the power provided by the supercontinuum laser enables measurements of overlay structures with opaque film layers.

A potential problem in overlay measurement is insufficient light penetration to the bottom grating. In many examples, there are non-transparent (i.e., opaque) film layers between the top and the bottom gratings. Examples of such opaque film layers include amorphous carbon, tungsten silicide (Wsix), tungsten, titanium nitride, amorphous silicon, and other metal and non-metal layers. Often, illumination light limited to wavelengths in the visible range and below (e.g., between 250 nm and 700 nm) does not penetrate to the bottom grating. However, illumination light in the infrared spectrum and above (e.g., greater than 700 nm) often penetrates opaque layers more effectively.

An effective target design or measurement structure propagates a non-zero diffraction order between the first pattern and the second pattern such that the relative positions of the two patterns affect the intensity of the out-going diffraction beam detected in the far field.

An operational definition of "opaque" in the ultra-violet and visible range is that the predicted precision for SCOL in the wavelength range of 250-700 nm is much worse than the required precision. This is due to attenuation of the propagating diffraction order carrying the relative position information between the first pattern and the second pattern. Measuring SCOL signals with illumination wavelengths greater than 700 nanometers (e.g., 800-1650 nm) improves SCOL precision when absorption is significantly less. In embodiments where illumination light having wavelengths greater than 700 nanometers is employed, the design pitch of the measurement target is selected such that there is usable SCOL signal.

Although several examples are described hereinbefore with reference to an scatteromety-based overlay measurement model, the methods and systems described herein may involve other process models (e.g., focus, dose, etch or deposition processing). The methods and systems described herein may also involve other metrology technologies (e.g. SEM, TEM, AFM, X-ray) to generate training and measurement data. Moreover, the methods and systems described herein are discussed with reference to scatterometry based metrology systems, but they can be also applied to other metrologies (e.g., imaging based metrology techniques).

In yet another aspect, the measurement model results described herein can be used to provide active feedback to a process tool (e.g., lithography tool, etch tool, deposition tool, etc.). For example, values of overlay error determined using the methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively.

In general, the systems and methods described herein can be implemented as part of the process of preparing a measurement model for off-line or on-tool measurement. In addition, both measurement models and any reparameterized measurement model may describe one or more target structures and measurement sites.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
   providing illumination light to a first plurality of measurement sites on a surface of a semiconductor wafer, wherein the first plurality of measurement sites include multiple layer structures having known overlay values;
   detecting an amount of light diffracted from each of the first plurality of measurement sites in response to the illumination light;
   generating a first amount of scatterometry data associated with measurements of the first plurality of measurement sites based on the detected amounts of light, the measurements performed by at least one scatterometry based metrology system;
   determining a plurality of principal features of the first amount of scatterometry data based on a transformation of the first amount of scatterometry data that reduces a dimension of the first amount of scatterometry data to generate a reduced amount of scatterometry data; and
   training a measurement model based on the plurality of principal features extracted from the first amount of scatterometry data as input to the measurement model and the known overlay values as output training data;
   determining an overlay value associated with each of a second plurality of measurement sites based on the trained measurement model; and
   communicating an indication of the overlay value to a semiconductor fabrication tool that causes the semiconductor fabrication tool to adjust one or more parameters of a fabrication process of the semiconductor fabrication tool to achieve a desired output from the fabrication tool.

2. The method of claim 1, wherein the transformation of the first amount of scatterometry data involves any of a principal component analysis (PCA), an independent component analysis (ICA), a kernel PCA, a non-linear PCA, a fast Fourier transform (FFT) analysis, a discrete cosine transform (DCT) analysis, and a wavelet analysis.

3. The method of claim 1, wherein the measurement model is any of a linear model, a polynomial model, a neural network model, a support vector machines model, a decision tree model, and a random forest model.

4. The method of claim 1, wherein the first amount of scatterometry data includes a combination of scatterometry measurements of a plurality of different metrology targets formed by the same process conditions.

5. The method of claim 1, wherein the first amount of scatterometry data includes scatterometry measurements acquired by a plurality of different metrology techniques.

6. The method of claim 1, wherein the first amount of scatterometry data includes scatterometry measurements associated with more than one target feature at any of the first plurality of sites.

7. The method of claim 1, wherein the transformation of the first amount of scatterometry data involves determining a difference between signals from scatterometry measurements of different targets, signals from scatterometry measurements acquired by different metrology techniques, or a combination of both.

8. The method of claim 1, wherein the transformation of the first amount of scatterometry data involves determining residuals of a fit of signals from scatterometry measurements of different targets to a first model, a fit of signals from scatterometry measurements of a target acquired by different metrology techniques to a second model, or a combination of both.

9. The method of claim 1, wherein the multiple layer structures at the first plurality of measurement sites on the surface of a semiconductor wafer are fabricated in accordance with design rules of a semiconductor fabrication process.

10. The method of claim 1, wherein the first plurality of sites on the surface of the semiconductor wafer include the known overlay values and known values of one or more additional parameters of interest, and wherein the training of the measurement model is also based on the known values of the one or more additional parameters of interest.

11. The method of claim 10, wherein the one or more parameters of interest includes any of a process parameter, a structural parameter, a dispersion parameter, and a layout parameter.

12. The method of claim 1, further comprising:
    providing illumination light to a second plurality of measurement sites on a surface of a semiconductor wafer, wherein the second plurality of measurement sites include multiple layer structures;
    detecting an amount of light diffracted from each of the second plurality of measurement sites in response to the illumination light;
    generating a second amount of scatterometry data associated with measurements of the second plurality of measurement sites based on the detected amounts of light, the measurements performed by the at least one scatterometry based metrology system;
    determining a plurality of principal features of the second amount of scatterometry data based on a transformation that reduces a dimension of the second amount of scatterometry data, wherein the determining of the overlay value associated with each of the second plurality of sites is based on a fitting of the plurality of principal features to the trained measurement model; and storing the overlay value in a memory.

13. A system comprising:

an illumination source configured to provide illumination light to a first plurality of measurement sites on a surface of a semiconductor wafer, wherein the first plurality of measurement sites include multiple layer structures having known overlay values;

a detector subsystem configured to detect an amount of light diffracted from each of the first plurality of measurement sites in response to the illumination light and generate a first amount of scatterometry data associated with measurements of the first plurality of measurement sites based on the detected amounts of light in accordance with at least one scatterometry based metrology technique; and a computing system configured to:
determine a plurality of principal features of the first amount of scatterometry data based on a transformation of the first amount of scatterometry data that reduces a dimension of the first amount of scatterometry data to generate a reduced amount of scatterometry data;

train a measurement model based on the plurality of principal features extracted from the first amount of scatterometry data as input to the measurement model and the known overlay values as output training data;

determine an overlay value associated with each of a second plurality of measurement sites based on the trained measurement model; and communicate an indication of the overlay value to a semiconductor fabrication tool that causes the semiconductor fabrication tool to adjust one or more parameters of a fabrication process of the semiconductor fabrication tool to achieve a desired output from the fabrication tool.

14. The system of claim 13, wherein the illumination source is configured to provide illumination light to the specimen at wavelengths greater than 700 nanometers, and the detector is configured to perform measurements of the target structure at wavelengths greater than 700 nanometers.

15. The system of claim 13, wherein the computing system is further configured to:

receive a second amount of scatterometry data associated with measurements of a second plurality of measurement sites having unknown overlay values, wherein the second amount of scatterometry data is derived from measurements performed in accordance with the same at least one scatterometry based metrology technique;

determine a plurality of principal features of the second amount of scatterometry data based on a transformation that reduces a dimension of the second amount of scatterometry data, wherein the determining of the overlay value associated with each of the second plurality of sites is based on a fitting of the plurality of principal features to the trained measurement model; and store the overlay value in a memory.

16. The system of claim 13, wherein the first amount of scatterometry data includes a combination of measurements of a plurality of different metrology targets formed by the same process conditions.

17. The system of claim 13, wherein the first amount of scatterometry data includes a combination of measurements acquired by a plurality of different metrology techniques.

18. The system of claim 13, wherein the multiple layer structures at the first plurality of measurement sites on the surface of a semiconductor wafer are fabricated in accordance with design rules of a semiconductor fabrication process.

19. A method comprising:

providing illumination light to a first plurality of measurement sites on a surface of a semiconductor wafer, wherein the first plurality of measurement sites include multiple layer structures;

detecting an amount of light diffracted from each of the first plurality of measurement sites in response to the illumination light;

generating a first amount of scatterometry data associated with measurements of the first plurality of measurement sites based on the detected amounts of light, the measurements performed by at least one scatterometry based metrology system;

determining a plurality of principal features of the first amount of scatterometry data based on a transformation that reduces a dimension of the first amount of scatterometry data to generate a reduced amount of scatterometry data;

determining an overlay value associated with each of the first plurality of sites based on a fitting of the plurality of principal features to a trained measurement model; and communicating an indication of the overlay value to a semiconductor fabrication tool that causes the semiconductor fabrication tool to adjust one or more parameters of a fabrication process of the semiconductor fabrication tool to achieve a desired output from the fabrication tool.

20. The method of claim 19, further comprising:

providing illumination light to a second plurality of measurement sites on a surface of a semiconductor wafer, wherein the first plurality of measurement sites include multiple layer structures having known overlay values;

detecting an amount of light diffracted from each of the second plurality of measurement sites in response to the illumination light;

generating a second amount of scatterometry data associated with measurements of the second plurality of measurement sites based on the detected amounts of light, the measurements performed by the at least one scatterometry based metrology system;

determining a plurality of principal features of the second amount of scatterometry data based on a transformation of the second amount of scatterometry data that reduces a dimension of the second amount of scatterometry data; and training the measurement model based on the plurality of principal features extracted from the second amount of scatterometry data and the known overlay values.

* * * * *